(12) United States Patent
Itoh (10) Patent No.: US 7,921,989 B2
(45) Date of Patent: Apr. 12, 2011

(54) SAMPLE CONVEYOR APPARATUS AND SAMPLE PROCESSING APPARATUS

(75) Inventor: Teruaki Itoh, Kumamoto (JP)

(73) Assignee: IDS Co., Ltd., Kumamoto-shi, Kumamoto (JP)

( * ) Notice: Subject to any disclaimer, the term of this patent is extended or adjusted under 35 U.S.C. 154(b) by 98 days.

(21) Appl. No.: 12/427,174

(22) Filed: Apr. 21, 2009

(65) Prior Publication Data

US 2009/0260457 A1 Oct. 22, 2009

(30) Foreign Application Priority Data

Apr. 21, 2008 (JP) ................................. 2008-110527

(51) Int. Cl.
*B67B 7/00* (2006.01)

(52) U.S. Cl. ....... 198/836.1; 422/65; 198/837; 198/841; 198/860.1

(58) Field of Classification Search ............... 198/836.1, 198/836.4, 837, 84, 860.1; 422/65
See application file for complete search history.

(56) References Cited

U.S. PATENT DOCUMENTS

| | | | | |
|---|---|---|---|---|
| 3,605,994 A | * | 9/1971 | Parlette | 8/861.1 |
| 3,848,732 A | * | 11/1974 | Catalano | 198/836.1 |
| 4,856,646 A | * | 8/1989 | Sjostrand | 198/836.1 |
| 5,316,134 A | * | 5/1994 | Donohue | 198/861.1 |
| 5,598,784 A | * | 2/1997 | Kubsik et al. | 104/111 |
| 5,730,276 A | * | 3/1998 | Itoh | 198/465.1 |
| 6,805,294 B2 | * | 10/2004 | Itoh | 235/462.01 |
| 7,159,489 B2 | * | 1/2007 | Itoh | 81/3.2 |
| 7,178,665 B2 | * | 2/2007 | Ryan | 198/860.1 |
| 7,207,241 B2 | * | 4/2007 | Itoh | 81/3.2 |
| 7,322,525 B2 | * | 1/2008 | Itoh | 235/462.43 |
| 7,392,949 B2 | * | 7/2008 | Itoh | 235/462.01 |
| 2007/0000352 A1 | * | 1/2007 | Itoh | 81/3.2 |

FOREIGN PATENT DOCUMENTS

| | | |
|---|---|---|
| JP | 10-242690 | 9/1998 |
| JP | 2005-263478 | 9/2005 |
| JP | 2007-50953 | 3/2007 |

OTHER PUBLICATIONS

Official Action in 2008-110527 dated Jan. 25, 2010 (mailed Feb. 2, 2010) and English translation.

* cited by examiner

*Primary Examiner* — Mark A Deuble
(74) *Attorney, Agent, or Firm* — Nixon & Vanderhye P.C.

(57) ABSTRACT

According to an aspect of the present invention, a sample conveyor apparatus for conveying a sample holder which permits a sample container to be held therein, the sample container permitting a sample to be received therein, includes, a belt base extending along a conveyance path, a conveyor belt stretched on the belt base and to be run to form the conveyance path, and a frame unit including a pair of guide rails which extend along the conveyance path to guide the sample holder along the conveyance path, the frame unit being detachable from the belt base, the conveyor belt being detachable from the belt base.

3 Claims, 11 Drawing Sheets

SAMPLE CONVEYOR APPARATUS AND SAMPLE PROCESSING APPARATUS

CROSS-REFERENCE TO RELATED APPLICATIONS

This application is based upon and claims the benefit of priority from prior Japanese Patent Application No. 2008-110527, filed Apr. 21, 2008, the entire contents of which are incorporated herein by reference.

BACKGROUND OF THE INVENTION

1. Field of the Invention

The present invention relates to a sample conveyor apparatus for conveying sample containers that can contain samples, such as blood samples, and a sample processing apparatus for processing such samples.

2. Description of the Related Art

A conveyor apparatus for conveying sample containers that can contain samples, such as blood samples is known, which comprises belt bases, along the length of which samples are conveyed, conveyor belts wound around the belt bases and movable in the circumferential direction of the belt bases, and a pair of guide rails provided on the top of each of the belt bases with a certain space defined therebetween (see, for example, Jpn. Pat. Appln. KOKAI Publication No. 2005-263478).

In this apparatus, sample holders, each of which includes a receiver for receiving a sample container and a groove formed in its outer surface, are placed on the belts, and are conveyed by the belts, engaged with the guide rails.

In the apparatus, however, each belt base and a corresponding frame portion are formed integral with each other, and hence the conveyor belts cannot be detached. This makes it difficult to repair or exchange the components of the apparatus.

BRIEF SUMMARY OF THE INVENTION

According to an aspect of the present invention, a sample conveyor apparatus for conveying a sample holder which permits a sample container to be held therein, the sample container permitting a sample to be received therein, comprises, a belt base extending along a conveyance path, a conveyor belt stretched on the belt base and to be run to form the conveyance path, and a frame unit including a pair of guide rails which extend along the conveyance path to guide the sample holder along the conveyance path, the frame unit being detachable from the belt base, the conveyor belt being detachable from the belt base.

According to another aspect of the present invention, a sample processing apparatus comprises, the sample conveyor apparatus, a sample processing unit provided along the conveyance path and configured to execute a preset process on the sample container or the sample, and a control unit configured to cause the sample processing unit to execute the preset process when the sample holder conveyed by the sample conveyor apparatus along the conveyance path passes the sample processing unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawing, which are incorporated in and constitute a part of the specification, illustrate embodiments of the invention, and together with the detailed description of the embodiments given below, serve to explain the principles of the invention.

DETAILED DESCRIPTION OF THE INVENTION

Figure 1:
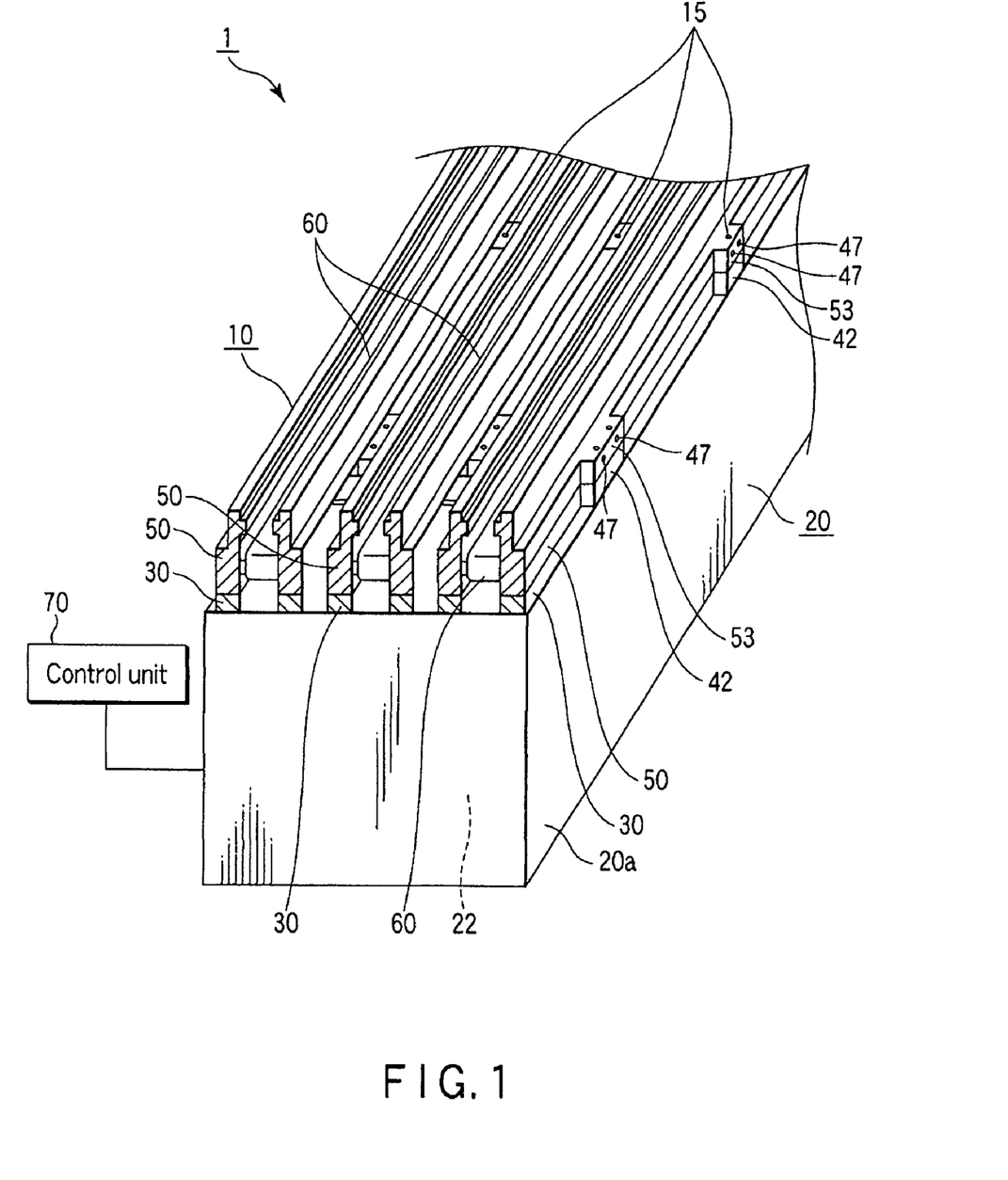
FIG. 1 is a perspective view illustrating a sample processing apparatus according to an embodiment of the invention.
Figure 2:
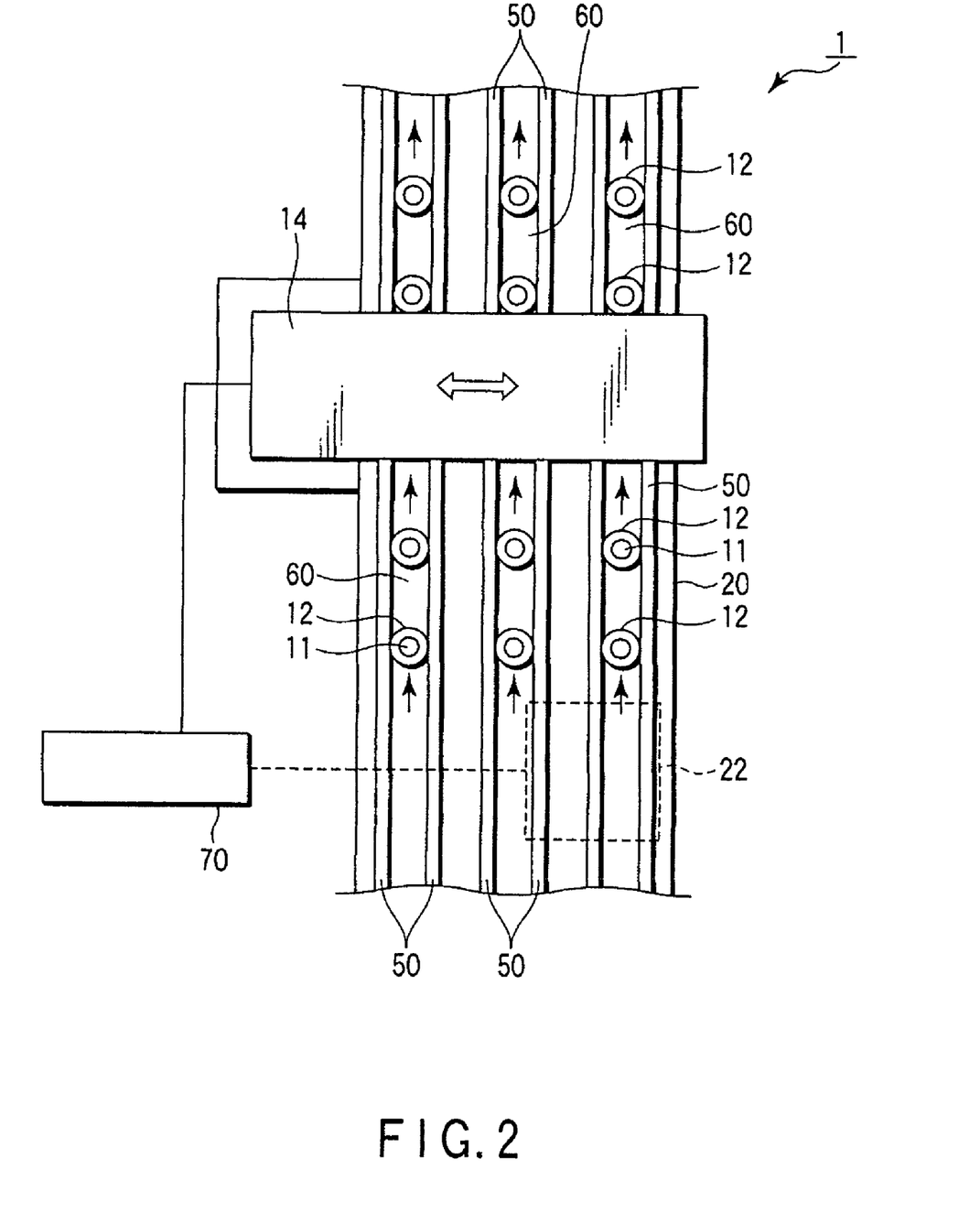
FIG. 2 is a plan view illustrating the sample processing apparatus of the embodiment.
Figure 3:
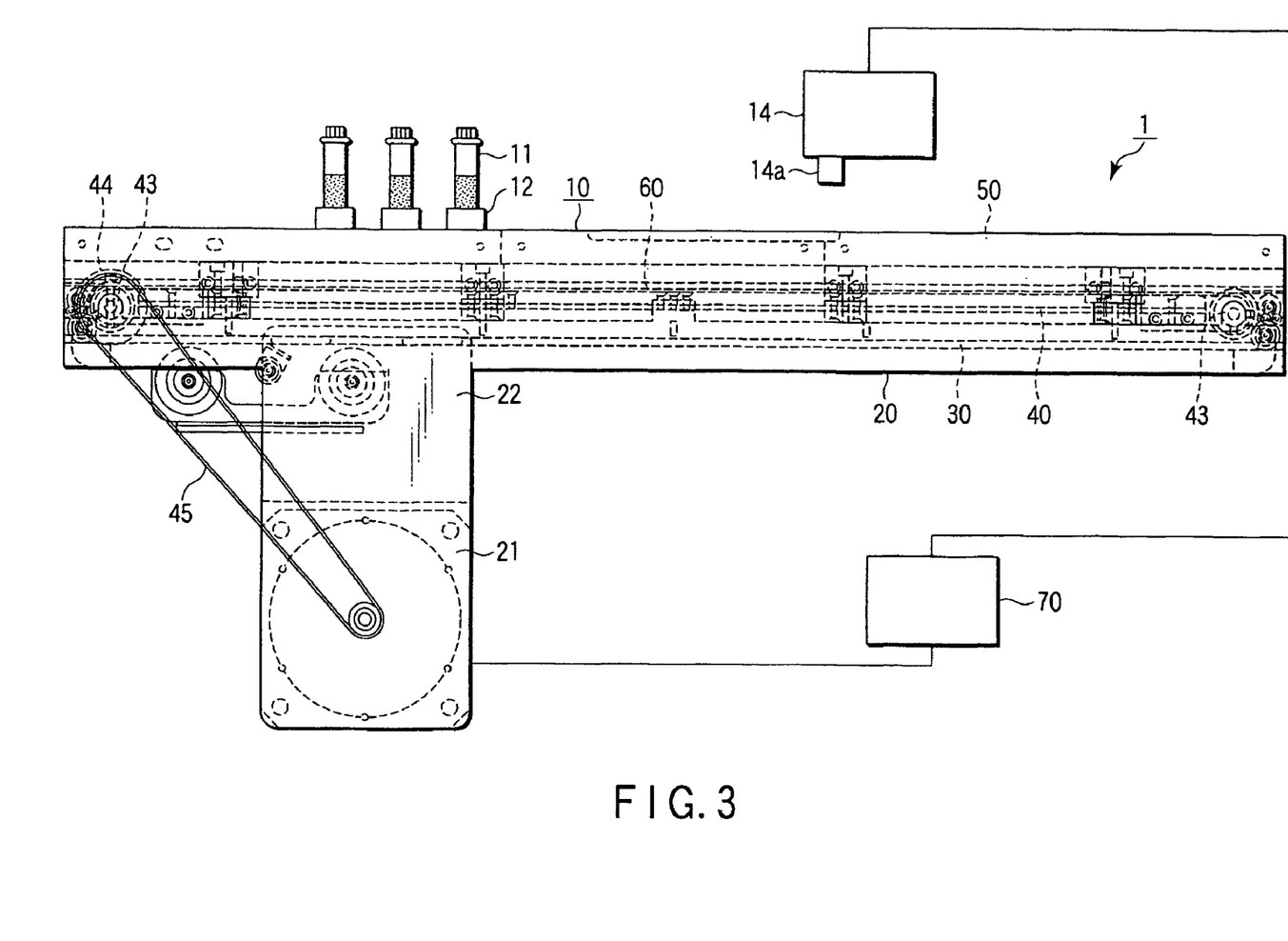
FIG. 3 is a side view illustrating the sample processing apparatus of the embodiment.
Figure 4:
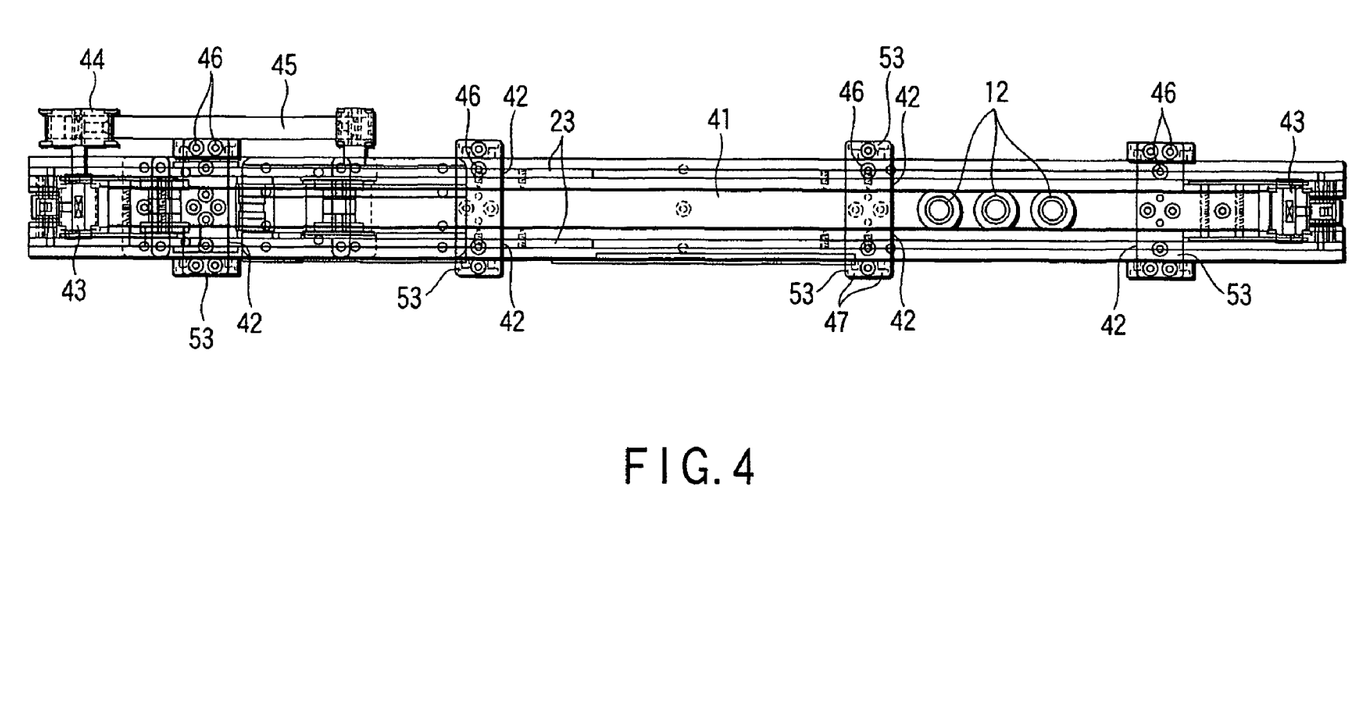
FIG. 4 is a plan view illustrating a sample conveyor apparatus according to the embodiment.
Figure 5:
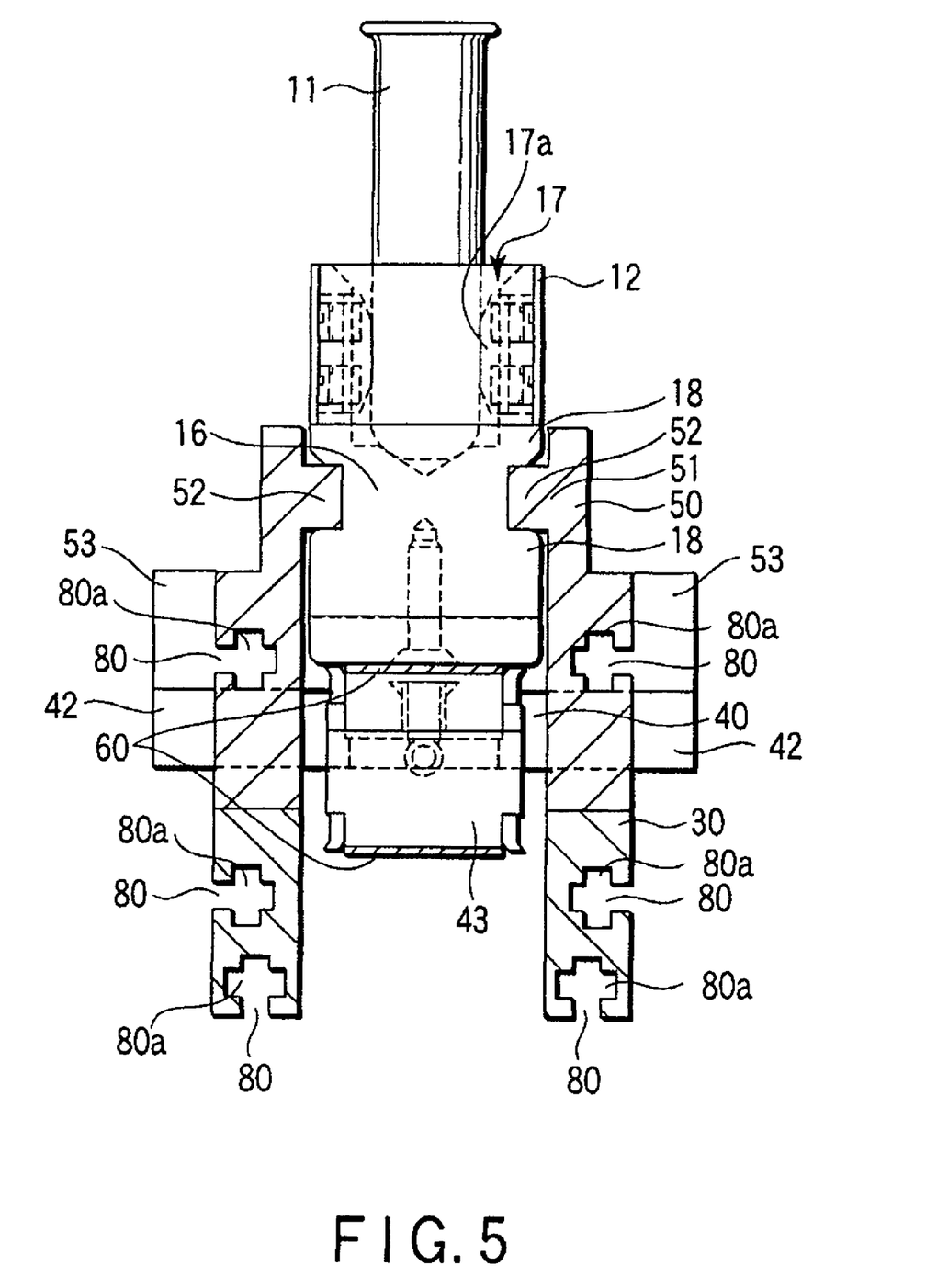
FIG. 5 is a sectional view illustrating the sample conveyor apparatus of the embodiment.

A sample processing apparatus 1 according to an embodiment of the invention will be described. FIG. 1 is a perspective view illustrating a sample conveyor apparatus 10 incorporated in the embodiment. FIG. 2 is a plan view illustrating the sample processing apparatus 1. FIG. 3 is a side view illustrating the sample processing apparatus 1. FIG. 4 is a plan view illustrating the sample conveyor apparatus 10. In these figures, the structure of the apparatus 1 is appropriately expanded, contracted or partially omitted for facilitating the explanation.

The sample conveyor apparatus 10 comprises: a support table 20 provided along a preset conveyance path; a plurality of base support members 30 extending in parallel on the support table 20; a plurality of belt bases 40 provided on the base support members 30; a plurality of frame units 50 provided on the belt bases 40 and each including a pair of guide rails 51 that extend along the length of the belt bases with a preset space defined therebetween; a plurality of conveyor belts 60 each stretched between the corresponding pair of guide rails 51 along the length of the rails; and a control unit (control means) 70 for controlling the operations. In FIG. 1, part of the cover 20a of the support table 20 is cut to show the internal structure of the table.

The sample conveyor apparatus 10 has a function of conveying sample containers 11 containing samples, such as blood samples, from one end to the other end in the convey direction indicated by the thin arrows shown in FIG. 2, along with respective sample holders 12, in accordance with the running of the conveyor belts 60.

Along the convey direction of the sample conveyor apparatus 10, a processing unit 14, such as an aliquoting/dispensing unit, for executing various processes on the samples is provided to form the sample processing apparatus 1. For example, the processing unit 14 includes a processing section movable in the direction in which it crosses the conveyor belts 60 as indicated by the thick arrow of FIG. 2. With this structure, the processing unit 14 isolates a sample from a certain sample container, and dispenses the same to another sample container. Alternatively, the processing unit 14 may execute a process on upstream-side and downstream-side sample containers successively conveyed by the same conveyor belt 60.

As shown in FIGS. 1 to 4, the support table 20 has a driving mechanism (driving means) at a lower portion thereof, which includes, for example, a motor 21 for forwarding the conveyor belts 60 at a preset speed. The support table 20 also has base support members 30 at an upper portion thereof.

Each base support member 30 comprises two slim members 23 extending parallel along the length thereof, and roller members 24 (see FIG. 11) opposing support rollers 43 described later. Two of the roller members 24 are provided at one of the longitudinal ends of each slim member 23, and the other two roller members 24 are provided at the other longitudinal end of each slim member 23. The belt bases 40 with the conveyor belts 60 stretched therebetween are received in a base reception portion 25 (see FIG. 11) formed between the slim members 23.

The belt bases 40 are received in the base reception portion 25, and each comprise a plate-like base main unit 41 extending along the conveyance path, a plurality of fixing blocks 42, support rollers 43 rotatably provided at the longitudinal opposite ends of the base main unit 41 and supporting the conveyor belts 60 from the reverse sides thereof, and a driving roller 44 coupled to the shaft of one of the support rollers 43. A transmission belt 45 is stretched between the driving roller 44 and the output shaft of the motor 21 to transmit the output of the motor 21 to the one support roller 43 via the driving roller 44.

Each belt base 40 has a preset width which enables each sample holder 12 to be mounted thereon, and has the corresponding endless conveyor belt 60 wound and stretched thereon, the belt 60 being run by the motor 21. When each conveyor belt 60 is run, the sample containers 11 placed thereon are conveyed along with their sample holders 12.

Outwardly projecting rectangular fixing blocks 42 are formed integral with the axially opposite ends of the base main unit 41 of each belt base 40. A plurality of similar fixing blocks (four fixing blocks in this embodiment) 42 are provided along the conveyance path.

Each fixing block 42 has a plurality of vertically elongated frame attaching holes 46 formed therein. The fixing blocks 42 provided at the axially opposite ends have a greater number of frame attaching holes 46 than the other frame attaching holes 42.

Figure 6:
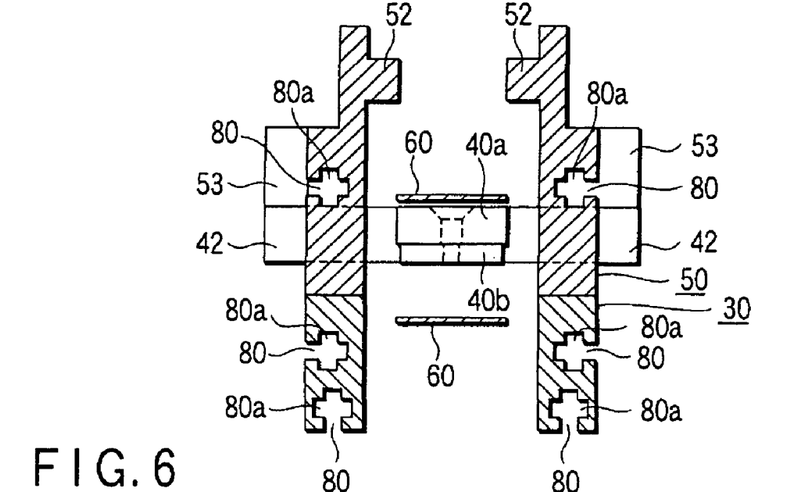
FIG. 6 is a sectional view illustrating a frame section and a base support section incorporated in the sample conveyor apparatus.
Figure 7:
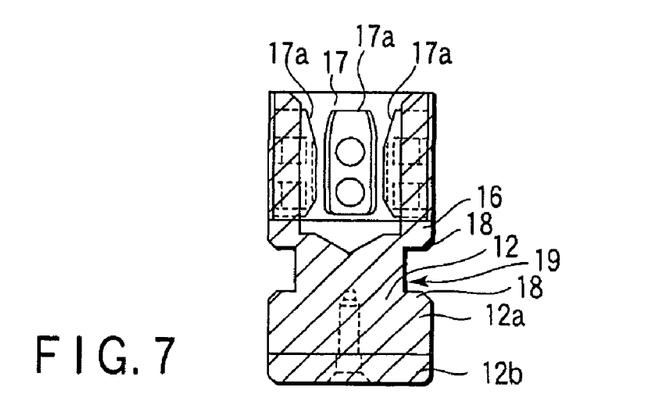
FIG. 7 is a sectional view illustrating a sample holder incorporated in the sample conveyor apparatus.
Figure 8:
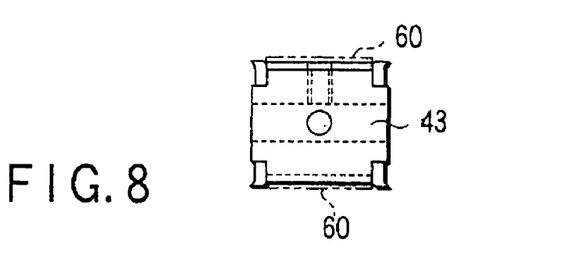
FIG. 8 is a side view illustrating a support roller incorporated in the sample conveyor apparatus.

The shafts of the support rollers 43 provided at the longitudinally opposite ends of each belt base 40 extend widthwise and project outwardly from the widthwise opposite ends of each belt base 40. When the shafts of the support rollers 43 are detachably attached to the longitudinally opposite ends of each base support member 30, the corresponding belt base 40 is supported by said each base support member 30. As shown in, for example, FIG. 6, each belt base 40 comprises an upper member 40a made of a resin, and a lower member 40b made of steel and coupled to the member 40a by bolts. Since the members of different materials are combined, the strength of each belt base 40 is enhanced.

Each frame unit 50 is fixed to the corresponding belt base 40, and is formed of, for example, a synthetic resin or aluminum. The two guide rails 51 of each frame unit 50 oppose each other at the opposite sides of the corresponding conveyor belt 60 to form an upper opening for receiving the sample holders 12, and are fixed to the corresponding belt base 40.

Projecting guide ribs (ribs) 52 to be engaged with an annular groove 19 formed in the flanges 18 of each sample holder 12 extend longitudinally on the inner sides of the guide rails 51 of each frame unit 50.

To-be-fixed blocks 53 corresponding to the fixing blocks 42 are formed integral with the widthwise extending outer sides of each pair of opposing guide rails 51. The to-be-fixed blocks 53 have vertically elongated base attaching holes 54 located corresponding to the engagement holes of the fixing blocks 42.

The lower portion of each frame unit 50 has a plurality of notches 50a and 50b (FIG. 9) located along the conveyance path. The notches 50a receive the fixing blocks 42. Namely, each belt base 40 is provided at the lower portion of the corresponding frame unit 50 between the two corresponding guide rails 51, and is widthwise outwardly protruded from the corresponding notch 50a such that it is superposed with the corresponding to-be-fixed block 53, described below.

Each to-be-fixed block 53 is superposed on the corresponding fixing block 42, whereby screw members 15 are inserted through the frame attaching holes 46 and the base attaching holes 54 to detachably attach the frame units 50 to the belt bases 40. Further, each to-be-fixed block 53 has attachment holes 47 formed therein for the corresponding base support member. The frame units 50 are connected to the base support members 30 via the attachment holes 47.

In addition, each to-be-fixed block 53 and each base support member 30 have longitudinally extending attachment channels 80. More specifically, attachment channels 80 are formed in the blocks 53 such that they open at their outer side surfaces, and are formed in the base support members 30 such that they open at their outer side surfaces and at their lower surfaces. Each attachment channel 80 has a cruciform cross section 80a. For example, if nuts are inserted in the channels 80 of the cruciform cross section 80a, and bolts are inserted into the nuts from the outside of the channels 80, arbitrary attachment mechanisms for attaching various components can be realized.

As shown in FIGS. 5 to 8, each sample holder 12 has a cylindrical base body 16. An upwardly opening receiving portion 17 is formed in the base body 16 along its axis. An elastically deformable holding portion 17a is provided on the inner peripheral surface of the receiving portion 17 for expanding/contracting the inner diameter of the receiving portion. A sample receptacle (test tube) 11 is vertically received and held in the receiving portion 17. Two flanges 18 are provided at the outer periphery of the base body 16 with a preset vertically space formed therebetween. Namely, an annular groove 19 (groove) is formed between the upper and lower flanges 18. The sample holder 12 comprises an upper member 12a of a resin, and a lower member 12b of a stainless steel coupled to the upper member 12a by a bolt, and has a high mechanical strength.

When the sample holder 12 is placed on one of the conveyor belts 60, a pair of parallel guide ribs 52 are engaged with the annular groove 19 formed between the two flanges 18, and the sample holder 12 is guided along the guide ribs 52.

Accordingly, when a plurality of sample holders 12 are placed on the conveyor belts 60 to engage their annular grooves 19 with the respective pairs of guide rails 51, and the motor 21 is rotated, the sample holders 12 are reliably conveyed by the conveyor belts 60 in a preset direction.

Further, when the sample containers 11 pass the processing position in the processing unit 14, the processing unit 14 executes various processes on the sample containers 11 or the samples therein under the control of the control unit 70.

Referring then to FIGS. 9 to 13, a description will be given of a method of attaching/detaching the sample conveyor apparatus 10 according to the embodiment.

Figure 9:
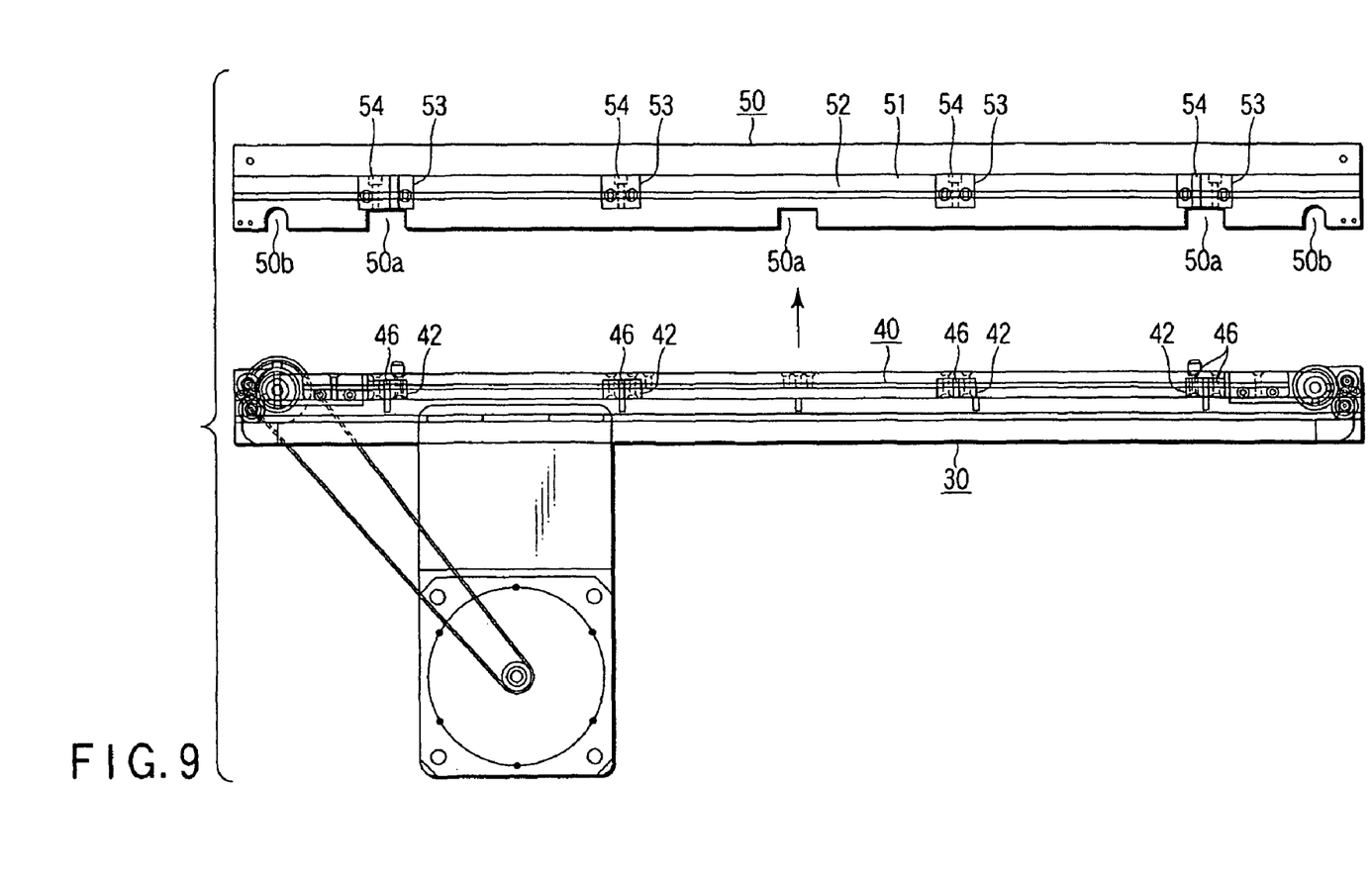
FIG. 9 is a side view useful in explaining the attachment/detachment procedures of the sample conveyor apparatus.
Figure 10:
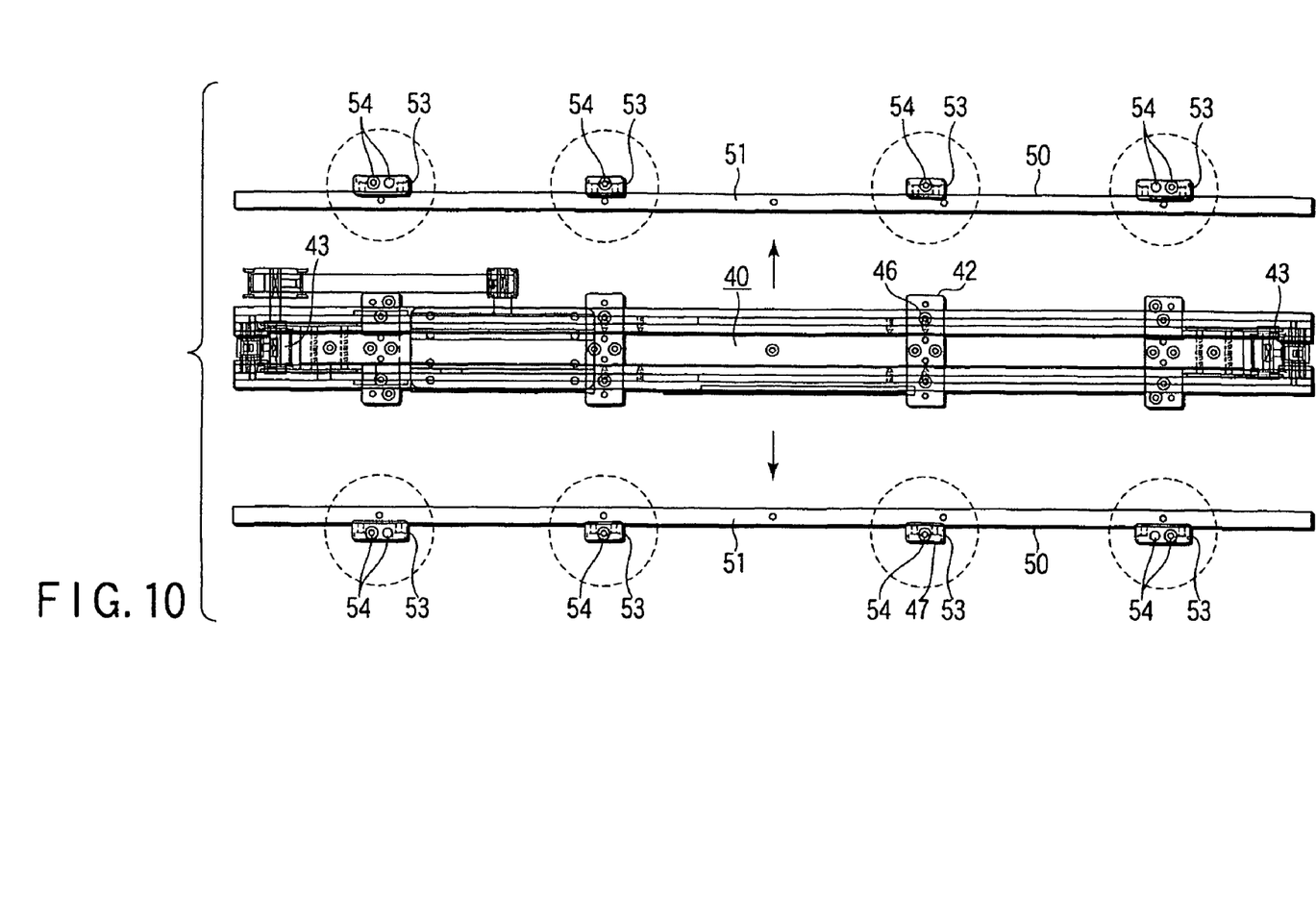
FIG. 10 is a plan view useful in explaining the attachment/detachment procedures of the sample conveyor apparatus.

Firstly, as shown in FIGS. 9 and 10, the screw members 15 as connection members in the fixing blocks 42 are unscrewed from the sample conveyor apparatus 10 shown in FIGS. 1 to 3, thereby detaching the to-be-fixed blocks 53 from the fixing blocks 42. As a result, the frame units 50 are detached from the belt bases 40.

Figure 11:
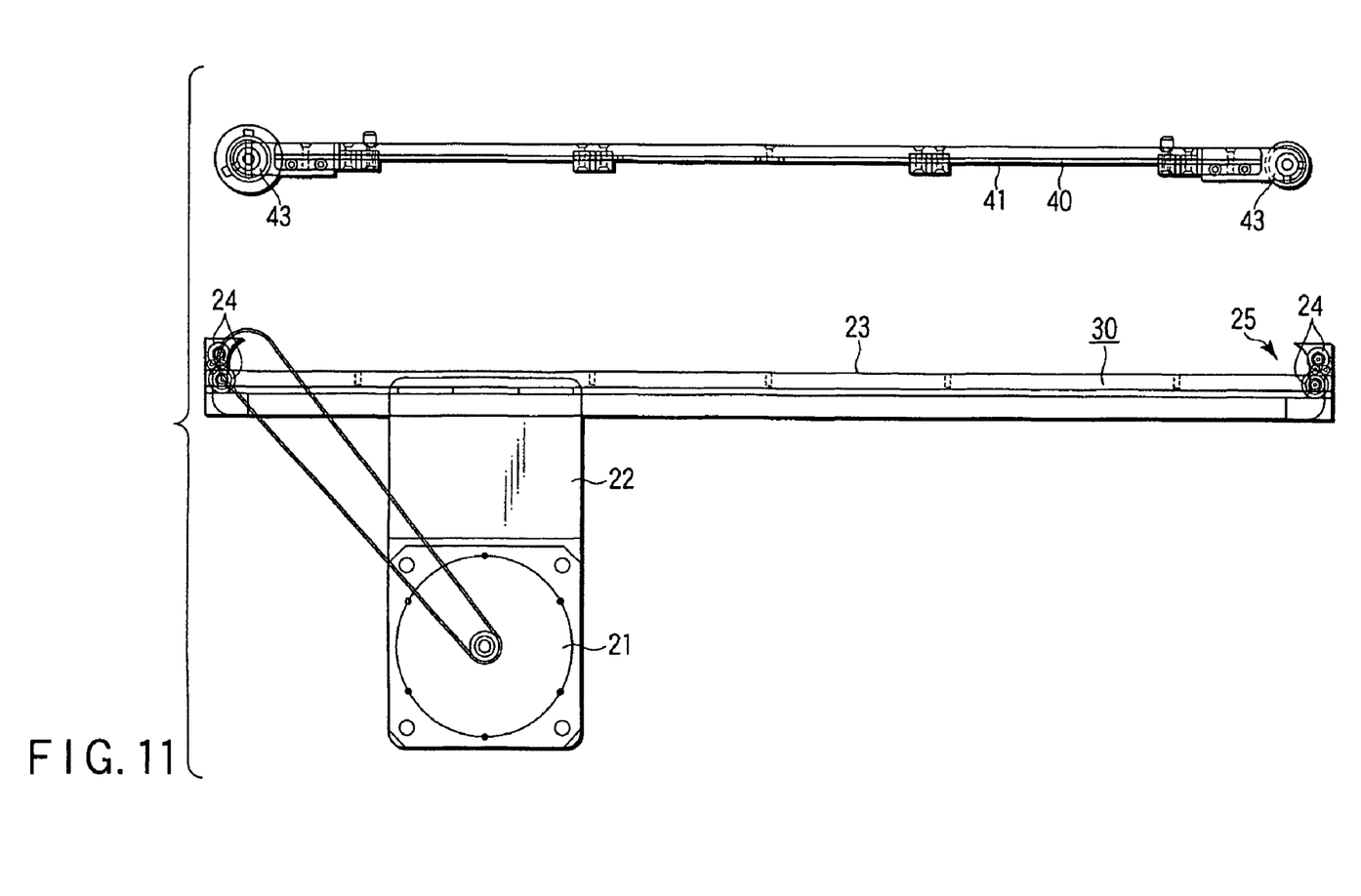
FIG. 11 is a side view useful in explaining the attachment/detachment procedures of the sample conveyor apparatus.
Figure 12:
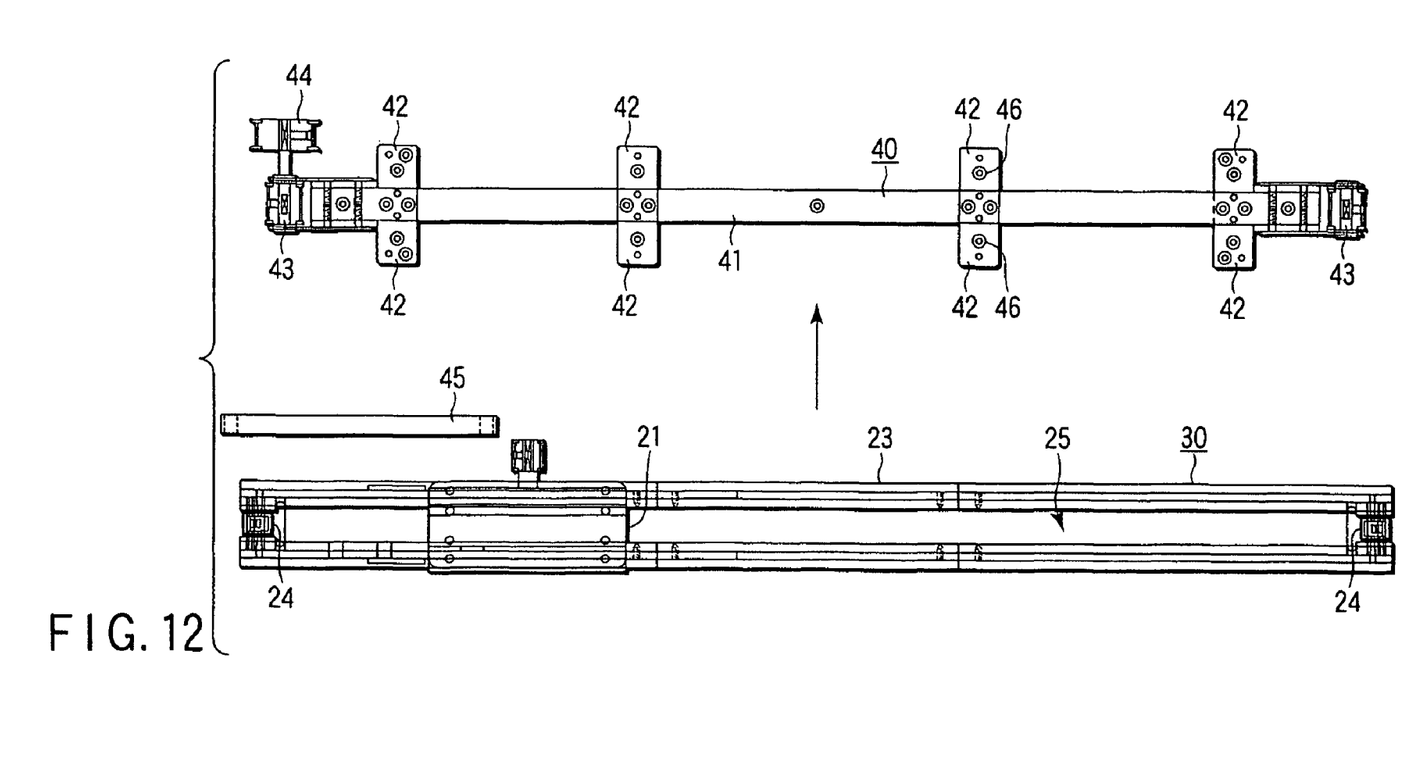
FIG. 12 is another plan view useful in explaining the attachment/detachment procedures of the sample conveyor apparatus.

Subsequently, as shown in FIGS. 11 and 12, the shafts of the roller members of the base bases 40 are detached from the base receiving portion, thereby detaching the base bases 40 from the base support members 30.

Figure 13:
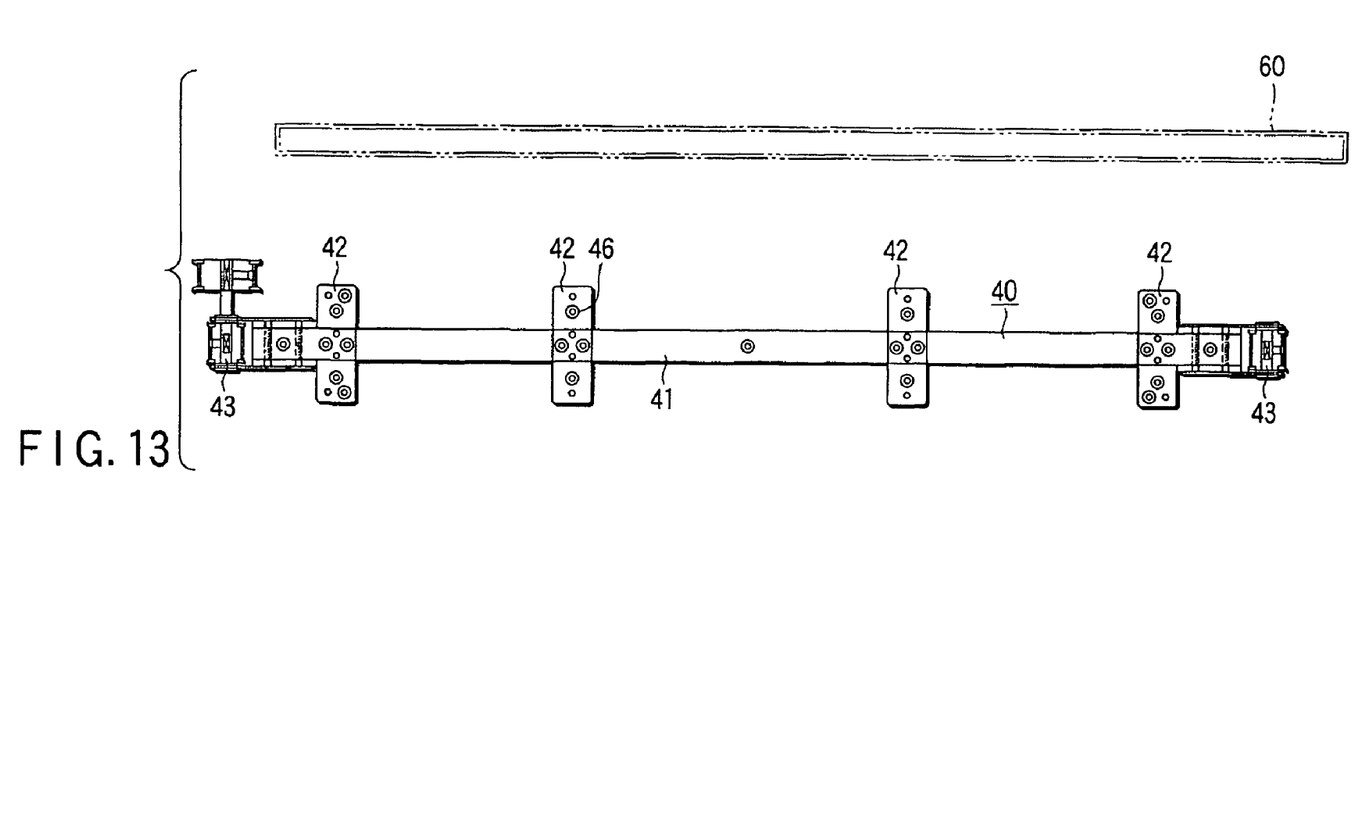
FIG. 13 is yet another plan view useful in explaining the attachment/detachment procedures of the sample conveyor apparatus.

After that, as shown in FIG. 13, the conveyor belts 60 stretched on the belt bases 40 are detached, which is the termination of the belt detachment work.

After exchange or repair work, the sample conveyor apparatus 10 can be assembled by the procedure opposite to the above.

The sample conveyor apparatus 10 of the embodiment can provide the following advantage: By virtue of the above structure, the conveyor belts can be easily detached, whereby repair of the apparatus and exchange of the components can be easily executed. Namely, since the conveyor belts 60, the belt bases 40, the frame units 50 and the base support members 30 are enabled to be attached to and detached from each other, belt exchange and repair works can be executed easily. Further, since the fixing blocks 42 and the to-be-fixed blocks 53 are provided and screwing is executed only in these blocks, assembly is executed easily and the attachment portions are strengthened.

The present invention is not limited to the above-described embodiment. For instance, although in the embodiment, the aliquoting/dispensing apparatus is employed as an example of a processing apparatus, another apparatus, such as an analysis apparatus, a label attaching apparatus, a carry-in apparatus, a carry-out apparatus, a bottle opener apparatus and a blood clot apparatus, may be employed in addition to or in place of the aliquoting/dispensing apparatus.

Furthermore, although in the above embodiment, the cylindrical sample holders 12 that hold respective sample containers 11 are conveyed, rack-type sample holders that each hold a plurality of sample containers 11 may be conveyed.

In addition, the structural elements of the invention may be modified in size, shape, etc., without departing from the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sample conveyor apparatus for conveying a sample holder which permits a sample container to be held therein, the sample container permitting a sample to be received therein, comprising:
   a belt base extending along a conveyance path;
   a conveyor belt stretched on the belt base and to be run to form the conveyance path;
   a frame unit including a pair of guide rails which extend along the conveyance path to guide the sample holder along the conveyance path,
   the frame unit being detachable from the belt base,
   the conveyor belt being detachable from the belt base;
   a base support member provided on a lower portion of the belt base, and including a base receiving portion which permits the belt base to be received therein, and running driving means which runs the conveyor belt;
   fixing blocks provided at widthwise opposite sides of the belt base and including a plurality of frame attachment holes; and
   to-be-fixed blocks provided on lower portions of the frame unit and including base attachment holes corresponding to the frame attachment holes, the to-be-fixed blocks being attachable to the fixing blocks,
   the belt base being detachable from the base support member.

2. The sample conveyor apparatus according to claim 1, wherein:
   the pair of guide rails includes ribs projecting toward each other;
   the sample holder includes a receiving portion which is an upper portion and permits the sample container to be received therein, and a groove formed in an outer periphery of a lower portion thereof and to be engaged with the ribs; and
   the sample container is received in the sample holder and conveyed along with the sample holder when the conveyor belt is run.

3. A sample processing apparatus comprising:
   the sample conveyor apparatus recited in claim 1;
   a sample processing unit provided along the conveyance path and configured to execute a preset process on the sample container or the sample; and
   a control unit configured to cause the sample processing unit to execute the preset process when the sample holder conveyed by the sample conveyor apparatus along the conveyance path passes the sample processing unit.

* * * * *